United States Patent
Hummel-Marquardt et al.

[11] Patent Number: 5,712,099
[45] Date of Patent: Jan. 27, 1998

[54] PROCESS FOR THE PRODUCTION OF ARABINONUCLEOSIDES

[75] Inventors: Heidi Hummel-Marquardt; Mario Kennecke; Alfred Weber; Thomas Schmitz; Ulf Tisltam; Klaus Nickisch, all of Berlin, Germany

[73] Assignee: Schering Aktiengesellschaft, Berlin, Germany

[21] Appl. No.: 737,735
[22] PCT Filed: Apr. 13, 1995
[86] PCT No.: PCT/EP94/01343
  § 371 Date: Jan. 17, 1997
  § 102(e) Date: Jan. 17, 1997
[87] PCT Pub. No.: WO95/32212
  PCT Pub. Date: Nov. 30, 1995

[30] Foreign Application Priority Data
May 20, 1994 [GB] United Kingdom ............ 44 18 474.3

[51] Int. Cl.$^6$ ............ C12Q 1/68; G01N 33/566; C07H 19/00; C07H 21/02
[52] U.S. Cl. ............ 435/6; 436/501; 536/22.1; 536/23.1; 536/24.1; 536/24.3; 536/25.3
[58] Field of Search ............ 435/6, 810; 436/501; 536/22.1, 23.1, 24.1, 24.3–24.33, 25.3; 935/72, 78

*Primary Examiner*—Ardin H. Marschel
*Assistant Examiner*—Jezia Riley
*Attorney, Agent, or Firm*—Millen, White, Zelano, & Branigan, P.C.

[57] ABSTRACT

The invention relates to a process for the production of arabinonucleosides of general formula I

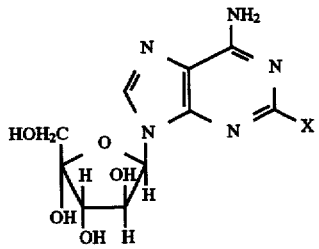

in which
  X represents a hydrogen atom or a fluorine atom,
from triacetates of general formula II

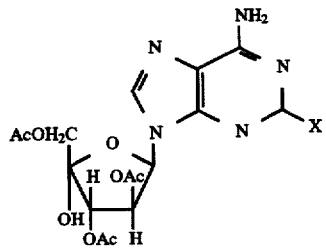

in which
  X has the above-mentioned meaning, and the groups
  Ac respectively mean acetyl groups,
which is characterized in that an esterase or lipase is caused to act on these compounds.

6 Claims, No Drawings

PROCESS FOR THE PRODUCTION OF ARABINONUCLEOSIDES

SUMMARY OF THE INVENTION

The invention relates as to a process for the production of arabinonucleosides of general formula I

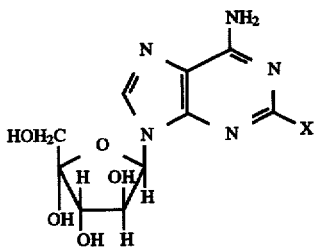

in which

X represents a hydrogen atom or a fluorine atom, from triacetates of general formula II

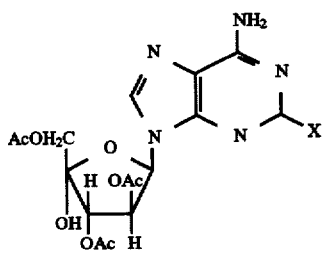

in which

X has the above-mentioned meaning, and the groups Ac respectively mean acetyl groups, which is characterized in that an esterase or lipase is caused to act on these compounds.

As is generally known, the arabinonucleosides of general formula I, 9β-D-arabinofuranosyl-9H-purine-6-amine (=vidarabine) and 9β-D-arabinofuranosyl-2-fluoro-9H-purine-6-amine (=fludarabine) are pharmacologically active substances that are distinguished by an antiviral and cytostatic action (EP-A 317,728 and WO 9209604).

According to the known prior art, these compounds can be produced from the triacetates of general formula II by reacting an ethanolic ammonia solution with said triacetates (J. Org. Chem. 33, 1968, 432 ff; Can. J. Cem. 59, 1981, 2608 ff and Nucleic Acids Symp. Ser. 1981, 9, 61 ff). This process is not only quite expensive, but it also has the drawback that heavily contaminated process products are obtained, especially in the synthesis of fludarabine.

In contrast, the process according to the invention can be implemented at relatively low cost and produces the desired process products with high purity.

The enzymatic hydrolysis of the triacetates of general formula II takes place quantitatively even at high substrate concentrations. This is surprising to one skilled in the art since it is fairly well known that acetates of multivalent alcohols often are only partially saponified enzymatically (Tetrahedron 46, 1990, 6587–6611).

The process according to the invention can be implemented with commercially available carboxylic acid esterases or lipases. Such are, for example, esterase from hog liver from the Fluka AG company; Ch-9470 Buche) with about 130 U/mg of protein (1 U corresponds to the amount of enzyme that reacts 1 μmol of butyric acid ethyl ester at 25° C. and pH 8.0), esterase from hog liver from the Boehringer-Mannheim company with about 130 U/mg of protein, esterase from hog liver from the Sigma Corp. company, St. Louis, USA with about 230 U/mg of protein, acylase I from *Aspergillus melleus* from the Sigma corp. company with about 0.5 U/mg of solid, lipase type II from the hog pancreas from the Sigma Corp. company with about 110–220 U/mg of prot. (olive oil substrate), lipase F7 from Mucor sp. from the Eurymatic Ltd. company, Cambridge.

To implement the process according to the invention, the substrate and enzyme are dissolved in a suitable buffer solution (citrate buffer, phosphate buffer, tris buffer, etc.) and shaken or stirred at 30° to 42° C. until complete reaction is accomplished. In this reaction 1 to 10 g of substrate and 1 to 100 mg of enzyme per l are normally used. After the reaction has been completed (which can be determined in a simple way by chromatography such as HPLC or TLC), the isolation of the process product can be isolated in a simple way by concentrating the reaction mixture by evaporation.

To be able to use the esterase several times, it is advisable to immobilize the latter in an already known way (Tetrahedron 26 (no4), pp. 407–410 (1985)) or to use a commercially available immobilized esterase (such as, for example, that on Eupergit® (immobilized esterase from hog liver from the Fluka AG company)) to implement the reaction.

The following embodiments are used to explain the process according to the invention in more detail.

EXAMPLES

Example 1

100 ml of 0.25 molar aqueous tris-(hydroxymethyl)-aminomethane/HCl buffer of pH 8.7 is mixed with 0.500 g of (2',3',5'-tri-O-acetyl-9β-D-arabinofuranosyl)-2-fluoro-9H-purine-6-amine and 0.1 mg of hog liver-esterase (Boehringer Mannheim; 130 U/mg of protein) and stirred for 70 hours at 37° C.

After HPLC, the reaction solution obtained is virtually free of 9β-D-arabinofuranosyl-2-fluoro-9H-purine-6-aminomonoacetate or -diacetate. It is concentrated by evaporation at a maximum bath temperature of 50° C. to about 5 ml, and the precipitated product is suctioned off, washed with water and dried in a vacuum at 100° C. 9β-D-Arabinofuranosyl-2-fluoro-9H-purine-6-aminine is obtained in a quantitative yield.

Example 2

Under the conditions of Example 1, 0.500 g of (2',3',5'-tris-O-acetyl-9β-D-arabinofuranosyl)-2-fluoro-9H-purine-6-amine and 0.1 mg of hog liver esterase (Sigma, Chem. St. Louis, USA 230 U/mg of protein) are reacted and worked up, and 9β-D-arabinofuranosyl-2-fluoro-9H-purine-6-amine is also obtained in a quantitative yield.

Example 3

Under the conditions of Example 1, but with the addition of 1.00 g of (2',3',5'-tris-O-acetyl-9β-D-arabinofuranosyl)-2-fluoro-9H-purine-6-amine, it is incubated for 200 hours. The reaction solution is worked up as described in Example 1, and 9β-D-arabinofuranosyl-2-fluoro-9H-purine-6-amine is also obtained in a quantitative yield.

Example 4 a) Eupergit® (Fluka AG) is mixed at a 10:1 ratio with hog liver esterase (Boehringer Mannheim; 130 U/mg of protein)

and 1 molar aqueous phosphate buffer of pH 7.5 and incubated for 3 days at room temperature. The product is then filtered, washed with phosphate buffer and distilled water and stored in 1 molar phosphate buffer of pH 7.5, which contains 0.05% benzoic acid ethyl ester.

b) 100 ml of 0.5 molar aqueous tris-(hydroxymethyl)-aminomethane/HCl buffer of pH 7.5 is mixed with 500 mg of (2',3',5'-tri-O-acetyl-9β-D-arabinofuranosyl)-2-fluoro-9H-purine-6-amine and 0.5 mg of immobilized hog liver esterase that is produced according to Example a, and it is incubated for 100 hours at 37° C. After this time, about 85% of the starting material has reacted.

The immobilizate is separated and can then be reused up to 30 times.

We claim:

1. A process for the production of arabinonucleosides of formula I

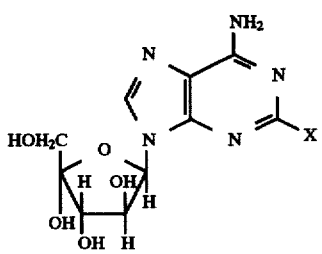

in which

X represents a hydrogen atom or a fluorine atom, comprising reacting a triacetate of formula II

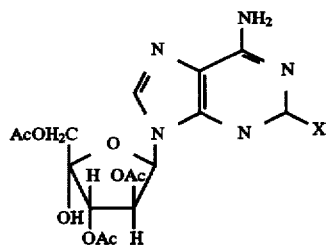

in which

X has the above-mentioned meaning, and the groups Ac respectively mean acetyl groups, with an esterase or lipase effective to hydrolyze the acetyl groups.

2. A process according to claim 1, wherein the esterase or lipase is hog liver esterase, acylase I from *Aspergillus melleus*, hog pancreas lipase type II or lipase F7 from Mucor sp.

3. A process according to claim 1, comprising combining the tryacylate and esterase or lipase in a buffer solution wherein reaction occurs in the mixture.

4. A process according to claim 3, comprising concentrating the mixture to isolate product.

5. A process according to claim 4, wherein the concentration is by evaporation.

6. A process for the production of a pharmaceutical composition, comprising reacting a triacetate of formula II

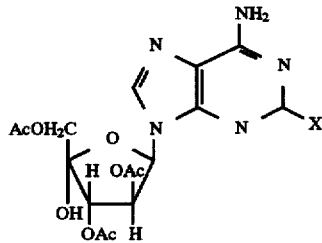

in which

X has the above-mentioned meaning, and the groups Ac respectively mean acetyl groups, with an esterase or lipase effective to hydrolyze the acetyl groups.

* * * * *